United States Patent [19]

Coffey et al.

[11] Patent Number: Plant 6,628

[45] Date of Patent: Feb. 21, 1989

[54] AVOCADO TREE CALLED THOMAS

[75] Inventors: Michael D. Coffey, Riverside; Fred B. Guillemet, Chino, both of Calif.

[73] Assignee: The Reagents of the University of California, Berkeley, Calif.

[21] Appl. No.: 99,440

[22] Filed: Sep. 21, 1987

[51] Int. Cl.[4] ..... A01H 5/03

[52] U.S. Cl. ..... Plt./44

[58] Field of Search ..... Plt./44

*Primary Examiner*—Robert E. Bagwill

*Attorney, Agent, or Firm*—Townsend and Townsend

[57] ABSTRACT

A new and distinct rootstock variety of avocado tree characterized by its high field resistance to Phytophthora root rot caused by *Phytophthora cinnamomi.* This variety has the highest level of resistance of any rootstock currently identified. It is characterized by relative ease of propagation using the etiolation method and graft compatibility with commercial scion varieties, including 'Hass', 'Gwen' 'Pinkerton', 'Fuerte', 'Bacon' and 'Zutano'.

1 Drawing Sheet

DESCRIPTION

This invention relates to a new and distinct rootstock variety of avocado tree (*Persea americana* var. drymifolia) designated 'Thomas'.

'Thomas' is a Mexican avocado tree recovered and asexually reproduced from the rootstock of a large Fuerte tree growing in Escondido, San Diego, Calif., which had been the subject of observations for root rot resistance. 'Thomas' has been tested at the University of California, Riverside and at South Coast Field Station, Irvine, Calif. for resistance to Phytophthora root rot caused by *Phytophthora cinnamomi.* It has also been tested for root rot resistance in various avocado groves in Southern California.

Figure 1:
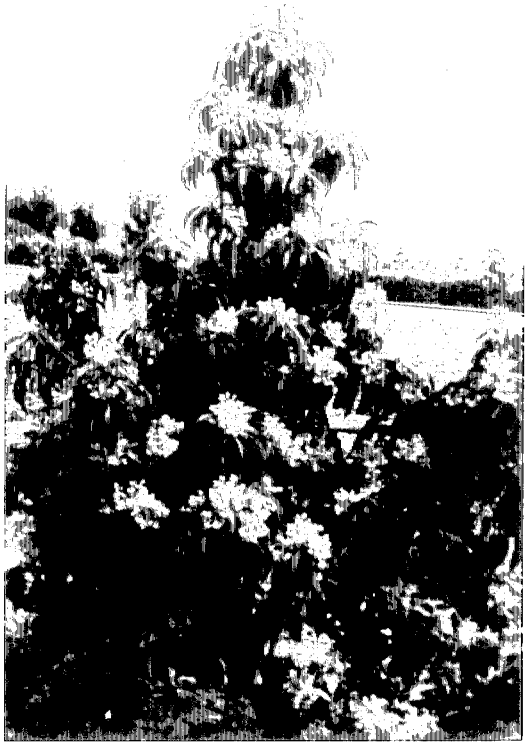
FIG. 1 shows the typical mature green fruit of the 'Thomas' variety, prior to ripening.
Figure 2:
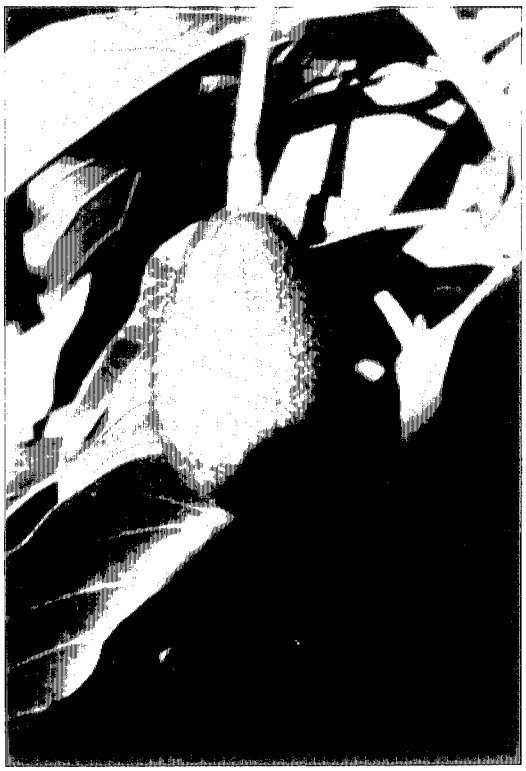
FIG. 2 shows the general shape and leaf color of the 'Thomas' selection.

'Thomas' has two primary characteristics that distinguish it. It has high field resistance to Phytophthora root rot. It is a Mexican variety and is well-adapted to California conditions.

Resistance to *Phytophthora cinnamomi* has been tested in many experiments with 'Thomas' in the field. 'Thomas' has consistently proved to be a superior rootstock with respect to Phytophthora root rot resistance. In an extremely severe test where the trees were deliberately inoculated with Phytophthora at planting time, 'Thomas' was evaluated as having the highest resistance among twelve selections tested. These selections included 'Duke 7', 'G755A', 'G755B', and 'Toro Canyon' which are currently available for commercial use.

TREES AND FOLIAGE

'Thomas', as is the case with the majority of avocado varieties, does not have distinctive foliage. The leaves have a distinct anise scent when crushed, which typifies the Mexican horticultural race.

FRUIT

Ovate; 150–200 grams. Typical Mexican type. Fruit color is purple with distinct speckling when ripe. With reference to the Munsell Color Charts typically 'Thomas' has a skin color (deep purplish red, Munsell Hue 7.5 RP 3/9). The season is about November through December.

The following chart represents ratings of the 'Thomas' variety compared with other root rot resistant varieties according to observations made at the Goleta Ranch Test Plot on May 30, 1985.

| SELECTION | TOTAL # TREES | AVERAGE GROWTH DIFF. | AVERAGE % GROWTH INCR. |
|---|---|---|---|
| DUKE 7 | 88 | 22.44 | 57.69 |
| G755C | 88 | 21.19 | 58.25 |
| TORO CANYON | 87 | 21.47 | 62.78 |
| D9 | 56 | 17.31 | 57.50 |
| G6 | 55 | 22.55 | 59.93 |
| THOMAS | 54 | 23.53 | 63.12 |
| G755A | 32 | 24.58 | 61.16 |
| G755B | 28 | 22.80 | 60.23 |
| G6#1 | 30 | 11.96 | 49.79 |
| BORCHARD | 30 | 18.74 | 59.66 |
| HUNTALAS | 24 | 11.42 | 42.07 |
| P1 | 23 | 14.40 | 52.98 |
| P.3 | 29 | 14.82 | 54.89 |
| P.6 | 27 | 14.10 | 50.87 |
| P.par | 11 | 18.17 | 59.97 |
| BARR | 21 | 18.65 | 55.68 |
| DUKE 6 | 18 | 17.54 | 56.05 |
| G1008 | 12 | 7.29 | 34.22 |

We claim:

1. The new and distinct rootstock variety of avocado tree herein described and illustrated and identified by the characteristics enumerated above.

* * * * *